United States Patent [19]

Pagano et al.

[11] Patent Number: 5,772,988
[45] Date of Patent: Jun. 30, 1998

[54] NAIL ENAMEL COMPOSITIONS FROM ACETOACETOXY METHACRYLATE COPOLYMER

[75] Inventors: Frank Charles Pagano, Avenel; Anjali Abhimanyu Patil, Westfield; Robert Walter Sandewicz, Spotswood, all of N.J.; Waifong Liew Anton; Harry Joseph Spinelli, both of Wilmington, Del.

[73] Assignee: Revlon Consumer Products Corporation, New York, N.Y.

[21] Appl. No.: 646,676

[22] Filed: May 10, 1996

[51] Int. Cl.$^6$ .................... A61K 7/04; A61K 7/043
[52] U.S. Cl. .................. 424/61; 424/78.03; 424/401; 514/772.4; 514/772.5; 514/772.6
[58] Field of Search ................... 424/61, 78.03, 424/40; 514/772.4, 772.5, 772.6

[56] References Cited

U.S. PATENT DOCUMENTS

| | | |
|---|---|---|
| 3,150,048 | 9/1964 | Hollub . |
| 3,554,987 | 1/1971 | Smith . |
| 3,721,555 | 3/1973 | Becker . |
| 3,728,314 | 4/1973 | Blank . |
| 4,100,125 | 7/1978 | Pezzuto . |
| 4,126,675 | 11/1978 | Boulogne . |
| 4,146,511 | 3/1979 | Moriya . |
| 4,158,053 | 6/1979 | Greene . |
| 4,166,110 | 8/1979 | Isobe . |
| 4,208,313 | 6/1980 | Lewis . |
| 4,229,431 | 10/1980 | Lee . |
| 4,235,768 | 11/1980 | Ritter . |
| 4,260,701 | 4/1981 | Lee, Jr. . |
| 4,316,929 | 2/1982 | McIntire . |
| 4,409,203 | 10/1983 | Gordon . |
| 4,425,326 | 1/1984 | Fuillon . |
| 4,430,367 | 2/1984 | Lat . |
| 4,626,428 | 12/1986 | Weisberg . |

(List continued on next page.)

FOREIGN PATENT DOCUMENTS

| | | |
|---|---|---|
| 89709 | 8/1994 | Australia . |
| 2118177 | 4/1995 | Canada . |
| 0214760 | 3/1987 | European Pat. Off. . |
| 568035 | 11/1993 | European Pat. Off. . |
| 626397 | 11/1994 | European Pat. Off. . |
| 634425 | 1/1995 | European Pat. Off. . |
| 650980 | 5/1995 | European Pat. Off. . |
| 697417 | 2/1996 | European Pat. Off. . |
| 229202 | 7/1985 | Japan . |
| 4103514 | 4/1992 | Japan . |
| 6279239 | 10/1994 | Japan . |
| 92558 | 10/1994 | Japan . |
| 252115 | 10/1995 | Japan . |
| 840833 | 2/1996 | Japan . |
| 2002013 | 2/1979 | United Kingdom . |
| 9210160 | 6/1992 | WIPO . |
| 9316133 | 8/1993 | WIPO . |
| 9421738 | 9/1994 | WIPO . |

OTHER PUBLICATIONS

Eastman Coatings Chemicals—CAP482—Esters in Nail Polish Feb. 1979.
Research Disclosure—Stahle Emulsion Polymers Jul. 1993.
Chem. Abstracts 122:322217w Mar. 1995.
Chem Abstracts 123: 17479u Apr. 1995.
Chem Abstracts 123: 17482a Mar. 1995.
Chem Abstracts 123: 40726f Apr. 1995.

*Primary Examiner*—Thurman K. Page
*Assistant Examiner*—S. Howard
*Attorney, Agent, or Firm*—Julie Blackburn

[57] ABSTRACT

A nail enamel composition comprising, by weight of the total composition:
10–95% solvent, and
5–90% of a copolymer resulting from the polymerization of monomer units A, B, and C wherein:

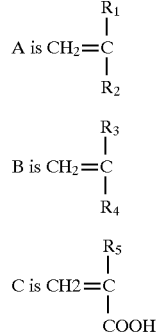

wherein $R_1$, $R_3$, and $R_5$ are each independently H, a $C_{1-30}$ straight or branched chain alkyl, aryl, aralkyl; $R_2$ is a pyrrolidone, or a substituted or unsubstituted aromatic, alicyclic, or bicyclic ring where the substitutents are $C_{1-30}$ straight or branched chain alkyl, or COOM wherein M is a $C_{1-30}$ straight or branched chain alkyl, pyrrolidone, or a substituted or unsubstituted aromatic, alicyclic, or bicyclic ring where the substituents are $C_{1-30}$ straight or branched chain alkyl

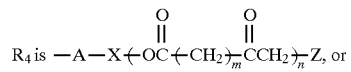

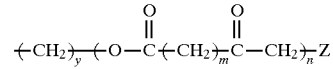

wherein

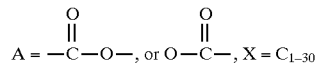

straight or branched chain alkyl, m is 1 to 5, n is 1 to 30, y is 0 to 50; and Z=H or a $C_{1-30}$ straight or branched chain alkyl, and a method and kit for coating the nails with said composition.

29 Claims, No Drawings

U.S. PATENT DOCUMENTS

| | | |
|---|---|---|
| 4,669,491 | 6/1987 | Weisberg . |
| 4,713,411 | 12/1987 | Kanou . |
| 4,954,559 | 9/1990 | Den Hartog . |
| 4,996,684 | 2/1991 | Say . |
| 5,057,312 | 10/1991 | Langla . |
| 5,093,108 | 3/1992 | Pappas . |
| 5,098,696 | 3/1992 | Montgomery . |
| 5,130,125 | 7/1992 | Martin . |
| 5,166,254 | 11/1992 | Nickle . |
| 5,182,327 | 1/1993 | Biale . |
| 5,219,560 | 6/1993 | Suzuki et al. ............................. 424/63 |
| 5,250,609 | 10/1993 | Kato . |
| 5,256,724 | 10/1993 | Biale . |
| 5,266,322 | 11/1993 | Myers . |
| 5,324,762 | 6/1994 | Overend . |
| 5,334,683 | 8/1994 | Kawanaka . |
| 5,346,977 | 9/1994 | Sakai . |
| 5,380,520 | 1/1995 | Dobbs . |
| 5,405,693 | 4/1995 | Dittrich . |
| 5,407,666 | 4/1995 | Patel . |

NAIL ENAMEL COMPOSITIONS FROM ACETOACETOXY METHACRYLATE COPOLYMER

TECHNICAL FIELD

The invention is in the field of compositions for application to fingernails and toenails.

BACKGROUND OF THE INVENTION

Traditional nail enamel compositions generally comprise a film former, a plasticizer, and a solvent. Cellulose derivatives, and in particular nitrocellulose, is most commonly used as a film former in commercial nail enamels because it is inexpensive and readily available. In addition, nail enamels containing cellulose-based film formers tend to provide good wear, adhesion, and gloss. However, nitrocellulose has certain undesireable features. For example, it is essentially gun cotton, an explosive, so its manufacture and transport prior to incorporation into nail enamel poses certain hazards. Moreover, in some cases nitrocellulose may yellow in the nail enamel as it ages.

Nail enamels based upon polymeric film formers are known in the art. Some of these nail enamels do not contain nitrocellulose, or contain it in much smaller amounts. However, in many cases, the polymeric film formers do not provide the wear, adhesion, and gloss which is desired for commercial preparations. Thus, the goal for cosmetics companies is to develop nail enamels based upon polymeric systems (preferably without nitrocellulose, or containing reduced amounts of nitrocellulose) which provide superior gloss, adhesion, and wear when compared to the currently available products.

One object of the invention is to provide a polymer-based nail enamel composition which provides good wear, adhesion, and gloss.

Another object of the invention is to provide a polymer-based nail enamel composition which can be made either without cellulose-based film formers, or containing significantly reduced levels of cellulose-based film formers.

Another object of the invention is to provide a method for forming a film on nails which is more resistant to wear when compared with normal methods and preparations.

BACKGROUND OF THE INVENTION

The invention is directed to a nail enamel composition comprising, by weight of the total composition:

10–95% solvent, and
5–90% of a copolymer resulting from the addition polymerization of monomer units A, B, and C wherein:

A is $CH_2=\underset{R_2}{\overset{R_1}{\underset{|}{\overset{|}{C}}}}$

B is $CH_2=\underset{R_4}{\overset{R_3}{\underset{|}{\overset{|}{C}}}}$

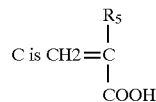

C is $CH_2=\underset{COOH}{\overset{R_5}{\underset{|}{\overset{|}{C}}}}$ wherein $R_1$, $R_3$, and $R_5$ are each independently H, a $C_{1-30}$ straight or branched chain alkyl, aryl, aralkyl; $R_2$ is a pyrrolidone, or a substituted or unsubstituted aromatic, alicyclic, or bicyclic ring where the substitutents are $C_{1-30}$ straight or branched chain alkyl, or COOM wherein M is a $C_{1-30}$ straight or branched chain alkyl, pyrrolidone, or a substituted or unsubstituted aromatic, alicyclic, or bicyclic ring where the substitutents are $C_{1-30}$ straight or branched chain alkyl.

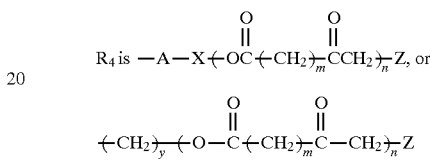

wherein

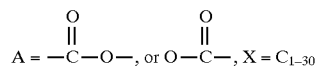

$X=C_{1-30}$ straight or branched chain alkyl, m is 1 to 5, n is 1 to 30, y is 0 to 50; and Z=H or a $C_{1-30}$ straight or branched chain alkyl.

The invention is also directed to a method for forming a film on a fingernail or toenail comprising:

a) applying to said nail a composition comprising, by weight of the total composition:
   10–95% solvent, and
   5–90% of a copolymer resulting from the addition polymerization of monomer units A, B, and C wherein:

A is $CH_2=\underset{R_2}{\overset{R_1}{\underset{|}{\overset{|}{C}}}}$

B is $CH_2=\underset{R_4}{\overset{R_3}{\underset{|}{\overset{|}{C}}}}$

C is $CH_2=\underset{COOH}{\overset{R_5}{\underset{|}{\overset{|}{C}}}}$ wherein $R_1$, $R_3$, and $R_5$ are each independently H, a $C_{1-30}$ straight or branched chain alkyl, aryl, aralkyl; $R_2$ is a pyrrolidone, or a substituted or unsubstituted aromatic, alicyclic, or bicyclic ring where the substitutents are $C_{1-30}$ straight or branched chain alkyl, or COOM wherein M is a $C_{1-30}$ straight or branched chain alkyl, pyrrolidone, or a substituted or unsubstituted aromatic, alicyclic, or bicyclic ring where the substitutents are $C_{1-30}$ straight or branched chain alkyl;

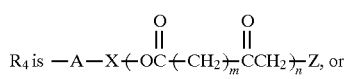

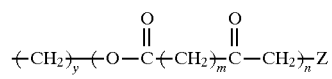

wherein

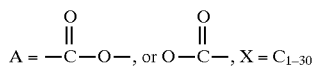

$X = C_{1-30}$ straight or branched chain alkyl, m is 1 to 5, n is 1 to 30, y is 0 to 50; and Z=H or a $C_{1-30}$ straight or branched chain alkyl.

The invention is also directed to a kit comprised of two containers, container 1 and container 2, wherein container I contains a nail enamel composition comprised of:
  10–95% solvent, and
  5–90% of a copolymer resulting from the polymerization of monomer units A, B, and C wherein:

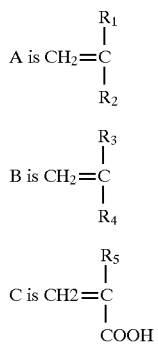

wherein $R_1$, $R_3$, and $R_5$ are each independently H, a $C_{1-30}$ straight or branched chain alkyl, aryl, aralkyl; $R_2$ is a pyrrolidone, or a substituted or unsubstituted aromatic, alicyclic, or bicyclic ring where the substitutents are $C_{1-30}$ straight or branched chain alkyl, or COOM wherein M is a $C_{1-30}$ straight or branched chain alkyl, pyrrolidone, or a substituted or unsubstituted aromatic, alicyclic, or bicyclic ring where the substitutents are $C_{1-30}$ straight or branched chain alkyl;

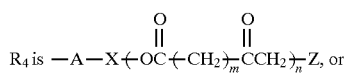

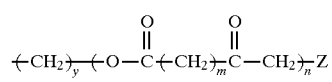

wherein

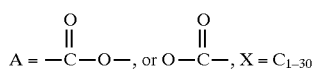

$X = C_{1-30}$ straight or branched chain alkyl, m is 1 to 5, n is 1 to 30, y is 0 to 50; and Z=H or a $C_{1-30}$ straight or branched chain alkyl.

and container 2 contains a composition comprising, by weight of the total composition:
  1–80% solvent,
  0.1–25% cellulose film former, and
  0.1–40% plasticizer.

DETAILED DESCRIPTION

THE SOLVENT

The nail enamel compositions of the invention comprise 10–95% by weight of the total composition, of solvent. The solvent may be aqueous or non-aqueous or a mixture of both types of solvents. Suitable non-aqueous solvents include aliphatic or aromatic ketones such as acetone, diacetone alcohol, dihydroxyacetone, ethyl butyl valerolactone, methyl ethyl ketone, and the like; aliphatic or aromatic alcohols such as methanol, propanol, benzyl alcohol, butoxyethanol, butoxypropanol, butyl alcohol, 3-methyl-3-methoxy-butanol, t-butyl alcohol, butylene glycol, diethylene glycol, abietyl alcohol, propylene carbonate, hexyl alcohol, isopropanol, and the like; glycol ethers; esters such as butyl acetate, ethyl acetate, etc.

THE COPOLYMER

The nail enamel compositions of the invention contain 5–90% by weight of the total composition of a copolymer resulting from the addition polymerization of monomer units A, B, and C wherein:

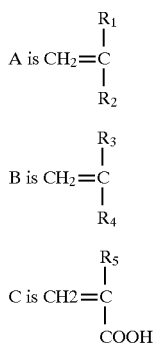

wherein $R_1$, $R_3$, and $R_5$ are each independently H, a $C_{1-30}$ straight or branched chain alkyl, aryl, aralkyl; $R_2$ is a pyrrolidone, or a substituted or unsubstituted aromatic, alicyclic, or bicyclic ring where the substitutents are $C_{1-30}$ straight or branched chain alkyl, or COOM wherein M is a $C_{1-30}$ straight or branched chain alkyl, pyrrolidone, or a substituted or unsubstituted aromatic, alicyclic, or bicyclic ring where the substitutents are $C_{1-30}$ straight or branched chain alkyl;

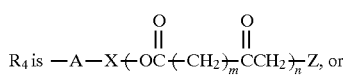

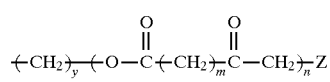

wherein

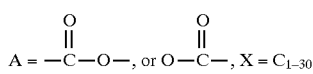

$X = C_{1-30}$ straight or branched chain alkyl, m is 1 to 5, n is 1 to 30, y is 0 to 50; and Z=H or a $C_{1-30}$ straight or branched chain alkyl.

The copolymers used in the compositions of the invention must be comprised of at least one A, one B, and one C monomer unit. The copolymer may contain only one type of A monomer unit, or the A monomer component may comprise a combination of two or more different A monomer units. For example, in the copolymer, the A component may comprise only methyl methacrylate, or it may comprise a combination of two or more monomer units such as methyl methacrylate, ethyl methacrylate, butyl methacrylate, and so on. In the same way, the final copolymer may contain only one type of B monomer, or it may contain a combination of two or more different types of B monomer units. In the same way, the final copolymer may contain only one type of C monomer unit, or it may contain a combination of two or more different types of C monomer units. The copolymer may also contain other types of monomer units in addition to A, B, and C, so long as at least the A, B, and C monomer units are present. Each unit provides a certain functional characteristic of the polymer, and it has been discovered that if the copolymer does not contain one or more of the units, the final nail enamel composition does not provide optimal wear. The A monomer component of the copolymer is believed to provide the film forming characteristics desired in a nail enamel formulation. The B monomer component is believed to provide an enhanced ability of the nail enamel composition to bind to the keratin of the nail. Finally, the C monomer component of the copolymer may assist in providing proper adhesion to the nail. It is prefered that the copolymer contains 30–95% of the A monomer units, 5–50% of the B monomer units, and 1–20% of the C monomer units. These percentages, and all percentages and ratios recited herein, unless otherwise noted, are based on weight amounts. The copolymers of the invention preferably have a number average molecular weight ranging from 20,000 to 100,000, preferably 27,000 to 53,000, and a weight average molecular weight ranging from 40,000 to 3,000,000, preferably 62,000 to 200,000, and glass transition temperature of 0°–50° C., preferably 5°–35° C.

Preferably, in the A monomer units, $R_1$ is hydrogen or a $C_{1-30}$, preferably a $C_{1-8}$ alkyl, and $R_2$ is a pyrrolidone, or a substituted or unsubstituted aromatic, alicyclic, or bicyclic ring where the substituents are $C_{1-30}$ straight or branched chain alkyl, or COOM wherein M is a $C_{1-30}$ straight or branched chain alkyl, pyrrolidone, or a substituted or unsubstituted aromatic, alicyclic, or bicyclic ring where the substituents are $C_{1-30}$ straight or branched chain alkyl. An example of an A monomer unit where $R_2$ is a pyrrolidone is vinyl pyrrolidone. Examples of A monomer units where $R_2$ is an unsubstituted aromatic ring are styrene and 2-methyl styrene. An example of an A monomer unit where $R_2$ is a substituted aromatic ring is vinyl toluene. In the preferred embodiment of the invention, $R_2$ in the A monomer unit is COOM where M is a straight or branched chain alkyl, pyrrolidone, or a substituted or unsubstituted aromatic, alicyclic, or bicyclic ring where the substituents are $C_{1-30}$ straight or branched chain alkyl. An example of an A monomer unit where $R_2$ is COOM and M is an alicyclic ring is cyclohexyl methacrylate. An example of an A monomer unit where $R_2$ is COOM and M is a bicyclic ring, in particular a substituted bicyclic ring, is isobornyl methacrylate. More preferably, in the A monomer units, $R_1$ is hydrogen or methyl, and $R_2$ is COOM where M is a $C_{1-8}$, preferably a $C_{1-4}$ alkyl. In one preferred embodiment of the invention, the A monomer units comprise a combination of two to three different types of A monomer units wherein $R_1$ is hydrogen or methyl and $R_2$ is COOM where M is a $C_{1-4}$ alkyl, for example a combination of methyl methacrylate and butyl methacrylate, a combination of methyl methacrylate, butyl acrylate, and butyl methacrylate, a combination of butyl acrylate and butyl methacrylate, and so on. Examples of copolymers containing such combinations of A monomer units include:

| A Monomer Unit | B Monomer Unit | C Monomer Unit |
|---|---|---|
| 10% methyl methacrylate<br>+<br>60% butyl methacrylate | 20% acetoactoxyethyl-methacrylate | 10% acrylic acid |
| 10% methyl methacrylate<br>+<br>5% butyl acrylate<br>+<br>55% butyl methacrylate | 20% acetoactoxyethyl-methacrylate | 10% acrylic acid |
| 5% butyl acrylate<br>+<br>65% butyl methacrylate | 20% acetoactoxyethyl-methacrylate | 10% acrylic acid |
| 40% methyl methacrylate<br>+<br>30% butyl methacrylate | 20% acetoactoxyethyl-methacrylate | 10% acrylic acid |
| 30% methyl methacrylate<br>+<br>40% butyl methacrylate | 20% acetoactoxyethyl- | 10% acrylic acid |

Most preferred is wherein the copolymer comprises only one type of A monomer unit as defined herein wherein $R_1$ is hydrogen or methyl, preferably methyl, and $R_2$ is COOM where M is a $C_{1-4}$ alkyl, preferably butyl, e.g. a copolymer consisting of about 70% butyl methacrylate, 20% acetoacetoxyethyl methacrylate, and 10% acrylic acid.

Preferably, in the B monomer units as defined herein, $R_3$ is hydrogen or a $C_{1-8}$ alkyl, preferably methyl, and $R_4$ is

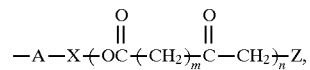

wherein

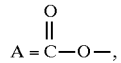

$X = C_{1-5}$ alkylene
$m = 1-5$,
$n = 1-5$, and
$Z = C_{1-10}$ straight chain alkyl.

More preferably, in the B monomer units as defined herein, $R_3$ is hydrogen or methyl, and $R_4$ is as defined above wherein:
$X = CH_2CH_2$
$m = 1$
$n = 1$
$Z = CH_3$ In the preferred embodiment of the invention the B monomer unit comprises acetoacetoxyethyl methacrylate.

Preferably, in the C monomer units, $R_5$ is hydrogen or a $C_{1-10}$ alkyl. More preferably, $R_5$ is hydrogen or methyl.

The copolymers used in the nail enamel compositions of the invention can be prepared by conventional polymerization techniques in which the monomers, solvent, and polymerization initiator are charged over a 1–24 hour period of time, preferably 2–8 hours, into a conventional polymerization reactor in which the constituents are heated to about 60°–1750° C., preferably 80°–1000° C. The polymer formed is a linear random polymer that has a weight average molecular weight of about 40,000 to 200,000 and a glass transition temperature of about 0°–50° C. The polymers may also be made by emulsion polymerization or suspension polymerization using conventional techniques.

Molecular weight is determined by gel permeation chromatography using polymethyl methacrylate as the standard. The glass transition temperature of the polymer is calculated according to the following formula:

$$1/Tg = W_1/Tg_1 + W_2/Tg_2 + W_3/Tg_3 + W_n/Tg_n$$

where Tg is the glass transition temperature of the polymer in degrees Kelvin; $W_1$, $W_2$, $W_3$ . . . $W_n$ are the weight fractions of each of the components of the polymer and $Tg_1$, $Tg_2$, $Tg_3$, $Tg_n$ are the Tg, in degrees Kelvin, of the homopolymer made from the individual components of the polymer. [Reference: T. G. Fox, Bull. Am. Phys. Soc., 1, No. 3, p. 123 (1956)].

Typical polymerization initiators that are used in the process are as follows: azo type initiators such as azo-bis-isobutyronitrile, 1,1'azo-bis(cyanocyclohexane), peroxy acetates such as t-butyl peracetate, peroxides such as di-t-butyl peroxide, benzoates such as t-butyl perbenzoates, octoates such as t-butyl peroctoate and the like. Typical solvents that can be used are ketones such as methyl amyl ketone, methyl isobutyl ketone, methyl ethyl ketone, aromatic hydrocarbons such as toluene, and xylene, alkylene carbonates such as propylene carbonate, n-methyl pyrrolidone, ethers, esters, acetate and mixtures of any of the above.

An aqueous composition can be formed from the acrylic polymer prepared by solution polymerization by stripping off the solvent and adding ammonia or amine and water preferably with some organic solvent to form an aqueous dispersion, hydrosol, or solution. An alternate method of forming an aqueous composition is to disperse the polymer into water or water/solvent mixtures with the aid of surfactants.

Higher molecular weight acrylic polymers can be formed by conventional emulsion polymerization techniques by emulsifying a mixture of monomer, water, surfactant, and polymerization catalyst and charging the resulting emulsion into a conventional polymerization reactor and heating the constituents in the reactor to about 60°–95° C. for about 15 minutes to about 8 hours. The resulting latex typically has a polymer solids content of about 10–40% of polymer dispersed in aqueous medium and the polymer has a weight average molecular weight of about 200,000 to 3,000,000. Typical catalysts used in the emulsion polymerization process are ammonium persulfate, hydrogen peroxide, sodium meta bisulfite, sodium sulfoxylate, and the like. Typical surfactants that may be used in the emulsion polymerization process are nonylphenoxypolyethyleneoxy ethanol sulfate, allyl dodecyl sulfosuccinate, alkyl phenoxy polyethylene oxyethanol, sodium lauryl sulfate, and mixtures thereof.

The acrylic polymer in an aqueous carrier may be neutralized with ammonia, typically ammonium hydroxide or an amine and the pH is adjusted to about 7 to 10. Useful amines are alkyl amines such as ethylamine, tertiary amines such as trimethylamine, triethylamine, dimethylaniline, diethylaniline, triphenylamine, dimethylethanol amine, triethanol amine, and the like.

The nail enamel compositions of the invention may be pigmented or clear. If pigmented, generally 0.1–30% by weight of the total composition, preferably 0.5–20%, more preferably 1–15% of pigment is suggested. Pigments suitable for use in nail enamel compositions are well known and include iron oxides, D&C and FD&C colors, titanium dioxide, and the like. The pigments may be treated or coated with agents which modify the surface properties such as silicones. Examples of silicone treated pigments which can be used in the compositions of the invention are set forth in U.S. Pat. No. 4,832,944, which is hereby incorporated by reference.

If the nail enamel compositions of the invention contain pigments, it is desireable to also incorporate 0.1–15% by weight of the total composition of a suspending agent which acts to suspend the pigments in the formulation. Suitable suspending agents are montmorillonite minerals and derivatives thereof, such as stearalkonium bentonite, hectorites, attapulgite, bentones, and the like, as well as polymeric compounds known as associative thickeners. Suitable associative thickeners generally contain a hydrophilic backbone and hydrophobic side groups. Examples of such thickeners include polyacrylates with hydrophobic side groups, cellulose ethers with hydrophobic side groups, polyurethane thickeners. Examples of hydrophobic side groups are long chain alkyl groups such as dodecyl, hexadecyl, or octadecyl; alkylaryl groups such as octylphenyl or nonyphenyl.

It may be desireable to add small levels of other film formers such as cellulosic film formers. Suitable cellulosic film formers include nitrocellulose, cellulose acetate isobutyrate, cellulose acetate propionate, and the like. If cellulosic film formers are added, a level of 0.1–15%, preferably 0.5–7%, more preferably 0.5–5% by weight of the total composition is suggested. The preferred embodiment of the invention is a nail enamel composition comprising:

10–95%, preferably 15–80%, more preferably 20–75% solvent,

5–90%, preferably 10–70%, preferably 15–60% of the copolymer, and 0.1–15%, preferably 0.5–7%, more preferably 0.5–5% of a cellulose-based film former, and, if the nail enamel is pigmented, 0.1–30% pigment.

It may also be desireable to include 0.1–20% by weight of the total composition, of a silicone glycol copolymer in the composition. Silicone glycol copolymers which may be used in the compositions of the invention are polymethylsiloxanes wherein a portion of the methylsiloxane units are substituted with polyalkylene glycol ether moieities. Preferred is wherein about 60–90% of the polymer (the percentage being based on the number of monomer units), of the compound is polydimethylsiloxane or polyhydrogen methylsiloxane and 30–40% of the compound (the percentage being based upon the number of monomer units) is di-methyl or hydrogen-methyl siloxane units substituted with polyalkylene glycol ethers. Most preferred are silicone glycol copolymers having a viscosity ranging from 1.0 to 500,000, preferably 1.0 to 2,000 centipoise at 25° C., a specific gravity ranging from 0.80 to 1.030 at 25° C., and comprise approximately 80% dimethylsiloxane units and 20% propylene oxide substituted methyl siloxane units. Silicone glycol copolymers having this description are commercially available from a variety of sources including Dow Corning under the tradenames Dow Corning Additive 3, 7, 11, 14, 18, 21, 24, 26, 28, 29, 51, 54, 56, 57, and 1248.

The compositions of the invention may also contain other ingredients such as emulsifiers, humectants, ancillary film formers, defoamers, plasticizers, preservatives, and the like.

The invention also comprises a method for forming a film on the fingernail or toenail by applying the compositions of the invention to the nail. The composition applied to the nails is allowed to dry for an appropriate period of time ranging from 60 seconds to 60 minutes. The resulting film exhibits improved wear. It may be desired to apply the composition of the invention to the nails, and then apply as a top coat, a composition which utilizes a cellulosic film former as the topcoat, or, in the alternative, to apply the cellulosic film former composition first to the nails and apply as a topcoat the composition of the invention. In any event, the composition of the invention and the cellulosic-based composition can be layered in any manner desired. In particular, the cellulose-based composition will generally comprise 1–80% of one or more of the solvents mentioned herein, 0.1–25% cellulose film former, and 0.1–40% plasticizer as a topcoat to said nails. Preferably the cellulose film former is nitrocellulose and the plasticizer is a glyceryl, glycol, or citrate ester as disclosed and claimed in U.S. Pat. No. 5,225,185 which is hereby incorporated by reference. By coating the nail with a combination of the nail enamel composition of the invention and the cellulose-based nail enamel, a film with superior wear characteristics is obtained.

The invention also is directed to a kit for applying nail enamel to the nails, said kit comprising two containers, container 1 and container 2. Container 1 contains the nail enamel composition of the invention, and container 2 contains a cellulose-based nail enamel composition mentioned above. Preferably one of the compositions is pigmented. The consumer who purchases the kit applies layers of each composition in the desired order. The combination provides signficantly improved wear. In the preferred embodiment, the composition of the invention is pigmented, and the cellulose-based composition is clear. The consumer applies the cellulose based composition as a basecoat and topcoat, and the pigmented composition of the invention as the middle, color coat.

The term "wear" indicates the overall resistance of the dried nail enamel film to chipping, loss of gloss, scratching, or other reduction in aesthetics due to tackiness of the coating or sensitivity of the coating to heat and moisture when on the nails.

The invention will be further described in connection with the following examples which are set forth for the purposes of illustration only.

EXAMPLE 1

Clear and pigmented enamel compositions were made as follows:

| Formula | w/w % | |
|---|---|---|
| | 1-1 | 1-2 |
| Polymer* | 37.80 | 25.70 |
| Butyl acetate | 21.30 | 31.00 |
| Butyl acetate | 38.10 | 31.30 |
| Pigment | 1.75 | — |
| Dimethicone copolyol | 0.10 | — |
| Stearalkonium bentonite | 0.95 | — |
| Isopropyl alcohol | — | 10.00 |
| Cellulose acetate propionate | — | 2.00 |

*Polymer: a polymer solution of 70% butyl methacrylate, 20% acetoacetoxyethylmethacrylate, 10% acrylic acid (60% solids). The polymer had a number average molecular weight of 44,000 and a weight average molecular weight of 102,000, a polydispersity of 2.3, and a glass transition temperature of about 15° C.

The compositions were made by combining the polymer, solvents, pigment, and other ingredients and mixing well.

EXAMPLE 2

Clear nail enamel compositions (base formulations) were made as follows:

| Formula | w/w % | | |
|---|---|---|---|
| | 2-1 | 2-2 | 2-3 |
| Stearalkonium bentonite | 1.05 | 1.05 | 1.05 |
| Polymer 1 | 60.00 | — | — |
| Polymer 2 | — | 58.82 | — |
| Polymer 3 | — | — | 60.00 |
| Dipropylene glycol dibenzoate | 2.00 | 2.00 | 2.00 |
| Butyl acetate | 17.83 | 19.01 | 17.83 |
| Isopropanol | 16.48 | 16.48 | 16.48 |
| Nitrocellulose | 2.64 | 2.64 | 2.64 |

Polymer 1: 50% solution in a 50/50 mixture of ethyl acetate and butyl acetate of a polymer comprised of 10% methyl methacrylate, 60% butyl methacrylate, 20% acetoacetoxyethyl methacrylate, and 10% acrylic acid.

Polymer 2: 51% solution in a 50/50 mixture of ethyl acetate and butyl acetate of a polymer comprised of 10% methyl methacrylate, 5% butyl acrylate, 55% butyl methacrylate, 20% acetoacetoxyethyl methacrylate, and 10% acrylic acid. The polymer had a weight average molecular weight of 176,000, a number average molecular weight of 49,200, a polydispersity of 3.6 and a glass transition temperature of 16° C.

Polymer 3: 50% solution in a 50/50 mixture of ethyl acetate and butyl acetate of a polymer comprised of 5% butyl acrylate, 65% butyl methacrylate, 20% acetoacetoxyethyl methacrylate, and 10% acrylic acid. The polymer had a weight average molecular weight of 187,000, a number average molecular weight of 55,000, and a glass transition temperature of 10° C.

EXAMPLE 3

Pigmented nail enamel compositions were made as follows:

| Formula | w/w % | | | |
|---|---|---|---|---|
| | 3-1 | 3-2 | 3-3 | 3-4 |
| Formula 2-1 (Example 2) | 89.95 | — | — | — |
| Formula 2-2 (Example 2) | — | 89.95 | — | — |
| Formula 2-3 (Example 2) | — | — | 89.95 | — |
| Nitrocellulose base* | — | — | — | 93.95 |
| Silicone glycol copolymer** | 0.10 | 0.10 | 0.10 | 0.10 |
| Pigment dispersion*** | 5.95 | 5.95 | 5.95 | 5.95 |
| Ethyl acetate | 4.00 | 4.00 | 4.00 | — |

*the formula for Nitrocellulose base is as follows:

| | w/w % |
|---|---|
| Nitrocellulose | 17.7 |
| Butyl acetate | 27.2 |
| Ethyl acetate | 27.0 |
| Isopropyl alcohol | 8.00 |
| Glyceryl tribenzoate | 13.1 |
| Stearalkonium bentonite | 1.00 |
| 2,5-dibutylphenyl-3,5-di-t-butyl-4-hydroxy-benzoate | 1.00 |
| Acetyl tributyl citrate | 4.00 |
| Glyceryl triacetate | 1.00 |

**Dow Corning 1248 Fluid, dimethyl, methyl hydrogen siloxane, reaction products with polypropylene glycol monoallyl ether.

***The formula for the pigment dispersion is as follows:

| | w/w % |
|---|---|
| Nitrocellulose | 7.15 |
| Acetyl tributyl citrate | 3.70 |

| | | |
|---|---|---|
| Ethyl acetate | 59.90 | |
| Butyl acetate | 9.45 | |
| Isopropyl alcohol | 1.50 | |
| Titanium dioxide | 14.15 | |
| Red iron oxide | 2.95 | |
| D&C red #7 calcium lake | 0.15 | |
| FD&C yellow #5 aluminum lake | 0.50 | |
| D&C red #6 barium lake | 0.60 | |

EXAMPLE 4

Formulas 3-2 and 3–4 of Example 3 were subjected to blind studies to ascertain the differences in performance characteristics. Test subjects applied Formula 3-2 to each of five nails and Formula 3–4 to the other five nails. Wear was evaluated by a test moderator on a scale of 1 to 10 with 10 being the best and 1 being the worst. The results after averaging are as follows:

| Day # | Formula 3-2 | Formula 3-4 |
|---|---|---|
| 1 | 10 | 9 |
| 2 | 8 | 6 |
| 3 | 5 | 3 |
| 4 | 3 | 1 |

It is seen that Formula 3-2, containing the polymers of the invention exhibit improved wear when compared with Formula 3–4 which does not contain the polymers of the invention.

EXAMPLE 5

Formulas 3—3 and 3–4 of Example 3 were subjected to blind studies to ascertain differences in wear characteristics. Test subjects applied Formula 3—3 to each of five nails, and Formula 3–4 to the other five nails. Wear was evaluated by a test moderator on a 1 to 10 scale, with 10 being the best and 1 being the worst. The results after averaging are as follows:

| Day # | Formula 3-3 | Formula 3-4 |
|---|---|---|
| 1 | 10 | 9 |
| 2 | 8 | 7 |
| 3 | 7 | 4 |
| 4 | 6 | 1 |

It is seen that Formula 3—3, containing an acrylate copolymer as called for by the invention, exhibits improved wear when compared with Formula 3–4 which is a nail enamel formulation not containing an acrylate copolymer as called for by the invention.

EXAMPLE 6

| Formula | 6-1 | 6-2 | 6-3 |
|---|---|---|---|
| Polymer 1* | 53.00 | — | — |
| Polymer 2* | — | 53.00 | — |
| Polymer 3* | — | — | 53.00 |
| Propylene glycol dibenzoate | 3.50 | 3.50 | 3.50 |
| Nitrocellulose | 2.64 | 2.64 | 2.64 |
| Stearalkonium bentonite | 1.05 | 1.05 | 1.05 |
| Butyl acetate | 38.33 | 38.33 | 38.33 |
| Formula | 6-1 | 6-2 | 6-3 |
| Isopropanol | 1.48 | 1.48 | 1.48 |

*Polymer 1 - contains 40% methylmethacrylate, 30% butylmethacrylate, 20% acetoacetoxyethylmethacrylate, and 10% acrylic acid as 50.3% solids in a solvent comprised of 80% ethyl acetate and 20% butyl acetate.
*Polymer 2 - contains 30% methylmethacrylate, 40% butylmethacrylate, 20% acetoacetoxyethylmethacrylate, and 10% acrylic acid as 50.4% solids in a solvent comprised of 80% ethyl acetate and 20% butyl acetate. The polymer had a weight average molecular weight of 93,000 and a number average molecular weight of 41,000, a polydispersity of 2.3 and a glass transition temperature of 35° C.
*Polymer 3 - contains 70% ethylmethacrylate, 20% acetoacetoxyethylmethacrylate, and 10% acrylic acid as 50% solids in a solvent comprised of 80% ethyl acetate and 20% butyl acetate.

Pigmented nail enamel compositions were made as follows:

| Formula | 6-4 | 6-5 | 6-6 |
|---|---|---|---|
| Formula 6-1 | 93.25 | — | — |
| Formula 6-2 | — | 88.60 | — |
| Formula 6-3 | — | — | 93.25 |
| Citric acid/malic acid/isopropanol* | 0.25 | 0.25 | 0.25 |
| Pigment dispersion*** | 6.40 | 6.20 | 6.40 |
| Silicone glycol copolymer** | 0.10 | 0.10 | 0.10 |
| Butyl acetate | | 4.85 | |

*a solution of 7.5% by weight citric acid, 2.5% by weight malic acid, and 90% by weight isopropanol
**Dow Corning 1248 Fluid, dimethyl, methyl hydrogen siloxane, reaction product with polypropylene glycol monoallyl ether.
***The formula for the pigment dispersion is as follows:

| | w/w % |
|---|---|
| Nitrocellulose | 16.55 |
| Acetyl tributyl citrate | 8.40 |
| Ethyl acetate | 24.50 |
| Butyl acetate | 24.65 |
| Isopropyl alcohol | 2.95 |
| Titanium dioxide | 5.40 |
| Red iron oxide | 7.55 |
| Black iron oxide | 4.15 |
| FD&C yellow #5 aluminum lake | 0.80 |
| D&C red #6 barium lake | 1.55 |
| D&C red #7 calcium lake (light) | 0.75 |
| D&C red #7 calcium lake (dark) | 2.50 |
| Ferric ammonium ferrocyanide | 0.25 |

EXAMPLE 7

Formulas 6-4, 6-5, and 6—6 from Example 6 were subjected to blind studies where these formulas were comparatively tested against a pigmented nail enamel not containing the acrylate copolymers of the invention, said comparative nail enamel having the following formula (Formula 7):

| | w/w % |
|---|---|
| Nitrocellulose | 15.50 |
| Butyl acetate | 23.80 |
| Ethyl acetate | 29.65 |
| Isopropyl alcohol | 7.00 |
| Glyceryl tribenzoate | 11.45 |
| Acetyl tributyl citrate | 3.50 |
| Glyceryl triacetate | 0.90 |
| Stearalkonium bentonite | 0.90 |

-continued

|  | w/w % |
|---|---|
| 2,5-dibutylphehyl-3,5-di-t-butyl-4-hydroxy-benzoate | 0.90 |
| Malic/citric acid/isopropanol* | 0.20 |
| Pigment dispersion** | 6.20 |

*a solution of 2.5% by weight malic acid, 7.5% by weight citric acid, and 90% by weight isopropanol.
**Pigment dispersion from Example 6.

In a blind study, Formula 6-4 was applied to alternate clean nails of 6 panelists and Formula 7 was applied to the other alternate nails so that each product was applied to 5 total nails per panelist. Immediately following application, panelists evaluated "application", "dry time" and "appearance" of their nails. Nail enamel wear was evaluated by a test moderator over 4 consecutive days. Wear was evaluated by the test moderator on a 1 to 10 scale with 10 being the best and 1 being the worst. The following results were obtained:

| Application | Ratio Found Satisfactory |
|---|---|
| Formula 6-4 | 6/6 |
| Formula 7 | 5/6 |
| Dry Time | |
| Formula 6-4 | 5/6 |
| Formula 7 | 6/6 |
| Appearance | |
| Formula 6-4 | 6/6 |
| Formula 7 | 6/6 |

| Scores for Resistance to Wear | | |
|---|---|---|
| Day # | Formula 6-4 | Formula 7 |
| 1 | 8 | 10 |
| 2 | 4 | 7 |
| 3 | 2 | 4 |
| 4 | 1 | 1 |

The above scores are after averaging.

In a blind study, Formula 6-5 was applied to alternate clean nails of 6 panelists and Formula 7 was applied to the other alternate nails so that each product was applied to 5 total nails per panelist. Immediately following application, panelists evaluated "application", "dry time" and "appearance" of their nails. Nail enamel wear was evaluated by the test moderator over 4 consecutive days. The following results were obtained:

| Application | Ratio Found Satisfactory |
|---|---|
| Formula 6-5 | 6/6 |
| Formula 7 | 6/6 |
| Dry Time | |
| Formula 6-5 | 4/6 |
| Formula 7 | 4/6 |
| Appearance | |
| Formula 6-5 | 6/6 |
| Formula 7 | 6/6 |

| Scores for Resistance to Wear | | |
|---|---|---|
| Day # | Formula 6-5 | Formula 7 |
| 1 | 9 | 10 |
| 2 | 8 | 9 |
| 3 | 7 | 6 |
| 4 | 6 | 5 |

Wear was evaluated by the test moderator on a 1 to 10 scale with 10 being the best and 1 being the worst. The above scores are averages.

In a blind study, Formula 6-6 was applied to alternate clean nails of 6 panelists and Formula 7 was applied to the other alternate nails so that each product was applied to 5 total nails per panelist. Immediately following application, panelists evaluated "application", "dry time" and "appearance" of their nails. Nail enamel wear was evaluated by the test moderator over 4 consecutive days. The following results were obtained:

| Application | Ratio Found Satisfactory |
|---|---|
| Formula 6-6 | 6/6 |
| Formula 7 | 3/6 |
| Dry Time | |
| Formula 6-6 | 6/6 |
| Formula 7 | 6/6 |
| Appearance | |
| Formula 6-6 | 6/6 |
| Formula 7 | 4/6 |

| Scores for Resistance to Wear | | |
|---|---|---|
| Day # | Formula 6-6 | Formula 7 |
| 1 | 9 | 9 |
| 2 | 7 | 9 |
| 3 | 4 | 6 |
| 4 | 2 | 3 |

Wear was evaluated by the test moderator on a 1 to 10 scale with 10 being the best and 1 being the worst. The above scores are averages.

EXAMPLE 8

A nail enamel formula was made as follows:

|  | w/w % |
|---|---|
| Polymer 1* (40% solids) | 58.7 |
| Water | 18.1 |
| Isopropyl alcohol | 8.8 |
| Methoxypropanol | 8.9 |
| Propylene carbonate | 1.0 |
| Succinate solution** | 3.0 |
| Diisopropyl sebacate | 0.5 |
| Propylene glycol dibenzoate | 0.5 |
| Tributoxyethyl phosphate | 0.5 |

*Polymer 1 contained 70% butylmethacrylate, 20% acetoacetoxyethyl methacrylate, and 10% acrylic acid neutralized with ammonium hydroxide. The copolymer was dissolved, the solution containing 30% water, 20% isopropyl alcohol, and 10% methoxypropanol.
**20 grams cellulose acetate butyrate succinate in methoxypropanol, mixed with 1.3 grams of a 28% w/w ammonium hydroxide solution.

In a blind study, the above formula was tested for wear on 5 panelists by applying the above formula to alternate nails and the nitrocellulose based comparative formula (as set forth in Example 3) to the remaining alternate nails. The wear results after averaging are shown as follows:

| | Wear | |
|---|---|---|
| Day # | Example 8 | Nitrocellulose Base |
| 1 | 9 | 10 |
| 2 | 7 | 7 |
| 3 | 6 | 5 |
| 4 | 6 | 3 |

Wear was evaluated by a test moderator on a scale of 1 to 10 with 10 being the best and 1 being the worst.

EXAMPLE 9

Nail enamel compositions were made as follows:

| | w/w % | | | |
|---|---|---|---|---|
| Formula | 9-1 | 9-2 | 9-3 | 9-4 |
| Polymer 1* | 38.80 | — | — | — |
| Polymer 2* | — | 27.40 | — | 30.80 |
| Polymer 3* | — | — | 29.50 | — |
| Nitrocellulose | 2.90 | 2.80 | 2.50 | 2.80 |
| Diisopropyl adipate | 1.90 | 1.80 | 1.60 | 1.80 |
| Stearalkonium bentonite | 1.00 | 1.00 | 0.90 | 1.00 |
| Butyl acetate | 11.80 | 35.80 | 32.70 | 32.80 |
| Ethyl acetate | 39.90 | 27.50 | 29.30 | 29.10 |
| Isopropyl alcohol | 1.50 | 1.50 | 1.30 | 1.50 |
| Silicone glycol copolymer** | 0.10 | 0.10 | 0.10 | 0.10 |
| Propylene carbonate | 1.00 | 1.00 | 1.00 | 1.00 |
| Acetyl tributyl citrate | 0.15 | 0.15 | 0.15 | 0.15 |
| Titanium dioxide | 0.25 | 0.25 | 0.25 | 0.25 |
| D&C Red #7, Ca Lake | 0.05 | 0.05 | 0.05 | 0.05 |
| Red iron oxide | 0.55 | 0.55 | 0.55 | 0.55 |
| Black iron oxide | 0.10 | 0.10 | 0.10 | 0.10 |

*Polymer 1 comprises 80% butyl methacrylate, 20% acetoacetoxyethylmethacrylate, the polymer had a weight average molecular weight of 47,900, a number average molecular weight of 25,100, a polydispersity of 1.91 and a glass transition temperature of 8° C.
*Polymer 2 comprises 70% butyl methacrylate, 20% acetoacetoxyethylmethacrylate, and 10% acrylic acid
*Polymer 3 comprises 80% butyl methacrylate, 10% acetoacetoxyethylmethacrylate, and 10% acrylic acid
**Dow Corning 1248 fluid, dimethyl, methyl hydrogen siloxane, reaction product with polypropylene glycol monoallyl ether.

In a blind study, Formula 9-1 was applied to alternate nails of six panelists and Formula 9-4 was applied to the remaining alternate nails so that each product was applied to 5 total nails per panelist. Immediately following application panelists evaluated "application", "dry time" and "appearance" of their nails. In addition, nail enamel wear was evaluated by a test monitor over 4 days. The results were as follows:

| | Ratio Found Satisfactory | Comments |
|---|---|---|
| Application | | |
| Formula 9-1 | 1/6 | 4 panelists preferred application of Formula 9-4 |
| Formula 9-4 | 4/6 | 2 panelists had no preference |
| Dry Time | | |
| Formula 9-1 | 6/6 | 4 panelists preferred application of Formula 9-4. |
| | Ratio Found Satisfactory | Comments |
|---|---|---|
| Formula 9-4 | 6/6 | 4 panelists said Formula 9-1 was stringy and difficult to apply. |
| Appearance | | |
| Formula 9-1 | 6/6 | 2 panelists preferred Formula 9-4 for appearance, other 4 |
| Formula 9-4 | 6/6 | panelists had no preference |

Total nail wear for Formulas 9-1 and 9-4 was evaluated as follows (after averaging):

| | Scores For Resistance To Wear | |
|---|---|---|
| Day # | Formula 9-1 | Formula 9-4 |
| 1 | 9 | 10 |
| 2 | 7 | 8 |
| 3 | 4 | 6 |
| 4 | 1 | 4 |

The above results illustrate that using polymers having less than the three monomer units A, B, and C disclosed and claimed provides less than optimal results.

EXAMPLE 10

A polymer of n-butyl methacrylate (BMA), 2-acetoacetoxyethyl methacrylate (AAEMA) and acrylic acid (AA) (weight ratio 70/20/10) was prepared by charging the following constitutents into a reactor equipped with a mechanical stirrer, thermometer and addition funnels:

Ethyl acetate, 117 grams; n-butyl methacrylate, 35 grams; 2-acetoacetoxyethyl methacrylate, 10 grams; and acrylic acid, 5 grams; were charged into the reactor. The contents of the reactor were brought to its reflux temperature. A solution of 2,2'-azobis(2,4-dimethylvaleronitrile), 0.25 grams in ethyl acetate, 5 grams; was injected into the reactor. Feed 1 (n-butyl methacrylate), 140 grams; 2-acetoacetoxyethyl methacrylate, 40 grams; and acrylic acid, 20 grams; was then started and added to the reactor over 60 minutes. Feed 2 (2,2'-azobis(2,4-diemthylvaleronitrile), 1.0 gram in ethyl acetate, 20 grams) was started at the end of Feed 1 and added to the reactor over the next 340 minutes. The mixture was held at its reflux temperature for another 30 minutes, then allowed to cool to room temperature.

The resultant polymer had a Tg (glass transition temperature) of about 15° C., a weight average molecular weight of 102,000 and number average molecular weight of 44,000 and polydispersity of 2.3. This polymer was used in formulating the nail enamel compositions of Example 1.

The other polymers of the Examples were prepared using the above mentioned procedure except that the solvent mixtures and monomer weights were varied to provide the desired polymer ratio.

EXAMPLE 11

An aqueous-based nail enamel composition was prepared as follows:

| | w/w % |
|---|---|
| Polymer Solution* | 75.00 |
| Water | 9.00 |
| Isopropyl alcohol | 11.50 |
| Dipropylene glycol methyl ether | 3.00 |
| Propylene glycol dibenzoate | 1.50 |

*Polymer is 50% butyl methyacrylate, 20% ethyl methacrylate, 20% acetoacetoxyethylmethacrylate, and 10% acrylic acid, (all percentages by weight), neutralized with ammonium hydroxide. The Polymer Solution contains 40% w/w Polymer and 60% w/w of a solution comprised (by weight of the total solution) of 30% water, 20% isopropyl alcohol, and 10% methoxypropanol.

The nail enamel composition of this Example 11 was tested for wear in a double blind study using the Nitrocellulose base of Example 3 as the control. The Example 11 nail enamel was applied to alternate nails of six panelists, and the Nitrocellulose base to the remaining alternate nails of the six panelists. Wear was evaluated by a test moderator every day for four days, by grading on a I to 10 scale with 10 being the best and 1 being the worst. The wear results, after averaging, are set forth below:

| Day # | Example 11 nail enamel | Nitrocellulose base |
|---|---|---|
| 1 | 10 | 9 |
| 2 | 9 | 7 |
| 3 | 8 | 5 |
| 4 | 6 | 2 |

EXAMPLE 12

A clear nail enamel composition was made as follows:

| | w/w % |
|---|---|
| Polymer Solution* | 86.7 |
| Water | 11.8 |
| 3-methyl-3-methoxy butanol | 1.5 |

*the Polymer is comprised of 70% butyl methacrylate, 20% acetoacetoxy ethylmethacrylate, and 10% acrylic acid. The Polymer solution is an anionic acrylic emulsion where the Polymer is present at a concentration of 34%.

We claim:

1. A nail enamel composition comprising, by weight of the total composition:
   10–95% solvent, and
   5–90% of a copolymer resulting from the addition polymerization of monomer units A, B, and C wherein:

$$A \text{ is } CH_2=C\begin{matrix}R_1\\|\\|\\R_2\end{matrix}$$

$$B \text{ is } CH_2=C\begin{matrix}R_3\\|\\|\\R_4\end{matrix}$$

$$C \text{ is } CH_2=C\begin{matrix}R_5\\|\\|\\COOH\end{matrix}$$

wherein $R_1$, $R_3$, and $R_5$ are each independently H, a $C_{1-30}$ straight or branched chain alkyl, aryl, aralkyl; $R_2$ is a pyrrolidone, or a substituted or unsubstituted aromatic, alicyclic, or bicyclic ring where the substitutents are $C_{1-30}$ straight or branched chain alkyl, or COOM wherein M is a $C_{1-30}$ straight or branched chain alkyl, pyrrolidone, or a substituted or unsubstituted aromatic, alicyclic, or bicyclic ring where the substitutents are $C_{1-30}$ straight or branched chain alkyl $$R_4 \text{ is } -A-X+OC+CH_2\}_m CCH_2\}_n Z, \text{ or}$$

$$+CH_2\}_y+O-C+CH_2\}_m C-CH_2\}_n Z$$

wherein $$A = -C-O-, \text{ or } O-C-, X = C_{1-30}$$

$X=C_{1-30}$ straight or branched chain alkyl, m is 1 to 5, n is 1 to 30, y is 0 to 50; and Z=H or a $C_{1-30}$ straight or branched chain alkyl.

2. The composition of claim 1 wherein the solvent comprises water.

3. The composition of claim 1 wherein the solvent is a non-aqueous solvent.

4. The composition of claim 3 wherein the non-aqueous solvent is acetone, diacetone alcohol, dihydroxyacetone, ethyl butyl valerolactone, methyl ethyl keton, methanol, propanol, benzyl alcohol, butoxyethanol, butoxypropanol, 3-methyl-3-methoxy-butanol, butyl alcohol, t-butyl alcohol, butylene glycol, diethylene glycol, abietyl alcohol, hexyl alcohol, isopropanol, ethyl acetate, butyl acetate, or mixtures thereof.

5. The composition of claim 1 wherein $R_1$ is hydrogen or a $C_{1-8}$ alkyl.

6. The composition of claim 5 wherein $R_1$ is hydrogen or methyl.

7. The composition of claim 1 wherein $R_2$ is COOM wherein M is a $C_{1-8}$ alkyl.

8. The composition of claim 7 wherein M is a $C_{1-4}$ alkyl.

9. The composition of claim 1 wherein $R_3$ is hydrogen or a $C_{1-8}$ alkyl.

10. The composition of claim 9 wherein $R_3$ is hydrogen or methyl.

11. The composition of claim 1 wherein $R_1$ is hydrogen or methyl, $R_2$ is $C_{1-4}$ alkyl, $R_3$ is hydrogen or methyl, $R_4$ is $$-A-X+OC+CH_2\}_m C-CH_2\}_n Z,$$

wherein $$A = C-O,$$

$X=C_{1-5}$ alkylene
m=1–5 alkylene,
n=1–5, and
$Z=C_{1-10}$ straight chain alkyl.

12. The composition of claim 1 wherein $R_1$ is hydrogen or methyl, $R_2$ is a $C_{1-4}$ alkyl, and $R_3$ is hydrogen or methyl.

13. The composition of claim 12 wherein $R_4$ is

wherein:
$X=CH_2CH_2$
$m=1$
$Y=CH_2$
$n=1$
$Z=CH_3$.

14. The composition of claim 1 wherein the A monomer unit comprises a combination of two or more different A monomer units.

15. The composition of claim 14 wherein the A monomer unit comprises at least two different monomer units selected from the group consisting of butyl acrylate, methylmethacrylate, butylmethacrylate, and ethylmethacrylate.

16. The composition of claim 1 wherein the copolymer comprises about 30–95% of the A monomer, 5–50% of the B monomer, and 1–20% of the C monomer.

17. The composition of claim 1 comprising, by weight of the total composition, 0.01–30% pigment.

18. The composition of claim 15 comprising, by weight of the total composition, 0.01–15% of a suspending agent.

19. The composition of claim 1 comprising, by weight of the total composition, 0.01–20% of a silicone glycol copolymer.

20. The composition of claim 16 wherein the copolymer comprises 70% of the A monomer, 20% of the B monomer, and 10% of the C monomer.

21. The composition of claim 16 wherein said copolymer comprises 70% butyl methacrylate, 20% acetoacetoxyethylmethacrylate, and 10% acrylic acid.

22. The composition of claim 1 additionally comprising, by weight of the total composition, 0.1–15% of a secondary film former.

23. The composition of claim 22 wherein the secondary film former is a cellulose film former.

24. The composition of claim 23 wherein the secondary film former is nitrocellulose.

25. A method for forming a film on a finger or toenail comprising:
  a) applying to said nail a composition comprising, by weight of the total composition:
    10–95% solvent, and
    5–90% of a copolymer resulting from the polymerization of monomer units A, B, and C wherein:

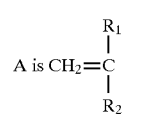

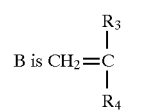

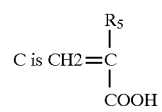

wherein $R_1$, $R_3$, and $R_5$ are each independently H, a $C_{1-30}$ straight or branched chain alkyl, aryl, aralkyl;

$R_2$ is a pyrrolidone, or a substituted or unsubstituted aromatic, alicyclic, or bicyclic ring where the substitutents are $C_{1-30}$ straight or branched chain alkyl, or COOM wherein M is a $C_{1-30}$ straight or branched chain alkyl, pyrrolidone, or a substituted or unsubstituted aromatic, alicyclic, or bicyclic ring where the substitutents are $C_{1-30}$ straight or branched chain alkyl

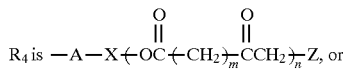

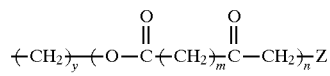

wherein

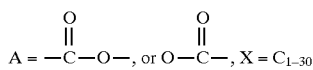

$X=C_{1-30}$ straight or branched chain alkyl, m is 1 to 5, n is 1 to 30, y is 0 to 50; and Z=H or a $C_{1-30}$ straight or branched chain alkyl.

26. The method of claim 25 further comprising applying at least one coat of a composition comprising 1–80% solvent, 0.1–25% cellulose film former, and 0.1–40% plasticizer.

27. The method of claim 26 where the coats are applied in any order.

28. A kit comprised of two containers, container 1 and container 2, wherein container 1 contains a nail enamel composition comprised of:
  10–95% solvent, and
  5–90% of a copolymer resulting from the polymerization of monomer units A, B, and C wherein:

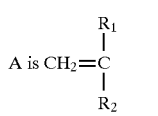

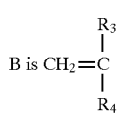

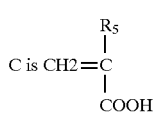

wherein $R_1$, $R_3$, and $R_5$ are each independently H, a $C_{1-30}$ straight or branched chain alkyl, aryl, aralkyl; $R_2$ is a pyrrolidone, or a substituted or unsubstituted aromatic, alicyclic, or bicyclic ring where the substitutents are $C_{1-30}$ straight or branched chain alkyl, or COOM wherein M is a $C_{1-30}$ straight or branched chain alkyl, pyrrolidone, or a substituted or unsubstituted aromatic, alicyclic, or bicyclic ring where the substitutents are $C_{1-30}$ straight or branched chain alkyl $R_4$ is 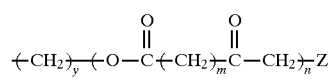, or

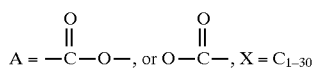

wherein $A = -\overset{O}{\underset{\|}{C}}-O-$, or $O-\overset{O}{\underset{\|}{C}}-$, $X = C_{1-30}$ $X = C_{1-30}$ straight or branched chain alkyl, m is 1 to 5, n is 1 to 30, y is 0 to 50; and Z=H or a $C_{1-30}$ straight or branched chain alkyl, and container 2 contains a composition comprising, by weight of the total composition:
1–80% solvent,
0.1–25% cellulose film former, and
0.1–40% plasticizer.

29. The kit of claim 27 wherein the composition in container 1 additionally comprises 0.1–30% by weight of the total composition of pigment.

* * * * *